US011242349B2

(12) United States Patent
Biemans et al.

(10) Patent No.: US 11,242,349 B2
(45) Date of Patent: Feb. 8, 2022

(54) ETHYNYL DERIVATIVES

(71) Applicant: Hoffmann-La Roche Inc., Little Falls, NJ (US)

(72) Inventors: Barbara Biemans, Basel (CH); Georg Jaeschke, Basel (CH); Antonio Ricci, Birsfelden (CH); Daniel Rueher, Raedersdorf (FR); Fionn O'Hara, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/865,233

(22) Filed: May 1, 2020

(65) Prior Publication Data
US 2020/0255440 A1  Aug. 13, 2020

Related U.S. Application Data

(63) Continuation of application No. 16/250,278, filed on Jan. 17, 2019, now abandoned, which is a continuation of application No. PCT/EP2017/067495, filed on Jul. 12, 2017.

(30) Foreign Application Priority Data

Jul. 18, 2016 (EP) .................... 16179837

(51) Int. Cl.
| C07D 401/10 | (2006.01) |
| C07D 471/10 | (2006.01) |
| C07D 487/10 | (2006.01) |
| C07D 491/107 | (2006.01) |
| C07D 491/20 | (2006.01) |
| A61K 31/517 | (2006.01) |
| A61P 25/16 | (2006.01) |

(52) U.S. Cl.
CPC ........ *C07D 487/10* (2013.01); *C07B 2200/07* (2013.01); *C07B 2200/09* (2013.01)

(58) Field of Classification Search
CPC .. C07D 401/10; C07D 471/10; C07D 487/10; C07D 491/107; C07D 491/20; A61K 31/527; A61P 25/16
See application file for complete search history.

(56) References Cited

U.S. PATENT DOCUMENTS

| 9,695,128 | B2 | 7/2017 | Biemans et al. |
| 9,725,416 | B2 | 8/2017 | Vieira et al. |
| 10,065,956 | B2 | 9/2018 | Biemans et al. |
| 10,189,848 | B2 | 1/2019 | Biemans et al. |
| 2008/0226618 | A1 | 9/2008 | Mansoor et al. |
| 2011/0124663 | A1 | 5/2011 | Conn et al. |
| 2011/0251169 | A1 | 10/2011 | Green et al. |
| 2012/0245153 | A1 | 9/2012 | Conn et al. |
| 2016/0207890 | A1 | 7/2016 | Biemans et al. |
| 2016/0362383 | A1 | 12/2016 | Vieira et al. |
| 2017/0008854 | A1 | 1/2017 | Biemans et al. |
| 2018/0002333 | A1 | 1/2018 | Biemans et al. |
| 2018/0134271 | A1 | 5/2018 | Okubo et al. |
| 2019/0119290 | A1 | 4/2019 | Biemans et al. |

FOREIGN PATENT DOCUMENTS

| WO | 2006/125784 A1 | 11/2006 |
| WO | 2008/151184 A1 | 12/2008 |
| WO | 2011/029104 A1 | 3/2011 |
| WO | 2011/051201 A1 | 5/2011 |
| WO | 2011/073172 A1 | 6/2011 |
| WO | 2011/128279 A1 | 10/2011 |
| WO | 2012/143340 A1 | 10/2012 |
| WO | 2012/146551 A1 | 11/2012 |
| WO | 2012/162635 A1 | 11/2012 |
| WO | 2013/045380 A2 | 4/2013 |
| WO | 2013/050454 A1 | 4/2013 |
| WO | 2014/060384 A1 | 4/2014 |
| WO | 2014/060394 A1 | 4/2014 |
| WO | 2014/124560 A1 | 8/2014 |
| WO | 2014/151784 A1 | 9/2014 |
| WO | 2014/195311 A1 | 12/2014 |
| WO | 2015/044075 A1 | 4/2015 |
| WO | 2015/104271 A1 | 7/2015 |
| WO | 2015/127872 A1 | 9/2015 |
| WO | 2015/128307 A1 | 9/2015 |
| WO | 2016/146600 A1 | 9/2016 |
| WO | 2017/009275 A1 | 1/2017 |

OTHER PUBLICATIONS

Battaglia, G. et al., "Pharmacological Activation of mGlu4 Metabotropic Glutamate Receptors Reduces Nigrostriatal Degeneration in Mice Treated with 1-Methyl-4-Phenyl-1,2,3,6-Tetrahydropyridine," J. Neuroscience 26(27):7222-7229 (2006).
Célanire, S. et al., "Recent Advances in the Drug Discovery of Metabotropic Glutamate Receptor 4 (mGluR4) Activators for the Treatment of CNS and non-CNS Disorders," Expert Opin. Drug Discov. 7(3):261-280 (2012).
Chang, H.J. et al., "Metabotropic Glutamate Receptor 4 Expression in Colorectal Carcinoma and Its Prognostic Significance," Clin. Cancer Res. 11(9):3288-3295 (2005).
Charvin, D. et al., "An mGlu4-Positive Allosteric Modulator Alleviates Parkinsonism in Primates," Mov. Disorders 33(10): 1619-1631 (2018).
International Preliminary Report on Patentability for PCT/EP2017/067495, dated Jan. 22, 2019, 8 pages.
International Search Report for PCT/EP2017/067495, dated Sep. 25, 2017, 6 pages.
Marino, M.J. et al., "Allosteric modulation of group III metabotropic glutamate receptor 4: A potential approach to Parkinson's disease treatment," Proc. Natl Acad. Sci. USA 100(23):13668-13673 (2003).
Niswender, C.M. et al., "Discovery, Characterization, and Antiparkinsonian Effect of Novel Positive Allosteric Modulators of Metabotropic Glutamate Receptor 4," Mol. Pharmacol. 74(5):1345-1358 (2008).

(Continued)

*Primary Examiner* — Bruck Kifle
(74) *Attorney, Agent, or Firm* — Andre T. Krammer

(57) ABSTRACT

The present invention relates to compounds that may be used in the treatment of Parkinson's disease, anxiety, emesis, obsessive compulsive disorder, autism, neuroprotection, cancer, depression or diabetes type 2.

4 Claims, 1 Drawing Sheet

(56) References Cited

OTHER PUBLICATIONS

Palucha, A. et al., "Group III mGlu receptor agonists produce anxiolytic- and antidepressant-like effects after central administration in rats," Neuropharmacology 46:151-159 (2004).

Pissimissis, N. et al., "The Glutamatergic System Expression in Human PC-3 and LNCaP Prostate Cancer Cells," Anticancer Res. 29(1):371-378 (2009).

Prediger, R.D.S. et al., "Anxiety in Parkinson's disease: A elitieal review of experimental and clinical studies," Neuropharmacology 62:115-124 (2012).

Stachowicz, K. et al., "AnxiolytiC-like effects of PHCCC, an allosteric modulator of mGlu4 receptors, in rats," Eur. J. Pharmacol. 498(1-3):153-156 (2004).

Uehara, S. et al., "Metabotropic Glutamate Receptor Type 4 Is Involved in Autoinhibitory Cascade for Glucagon Secretion by α-Cells of Islet of Langerhans," Diabetes 53(4):998-1006 (2004).

International Preliminary Report on Patentability for PCT/EP2015/050127, dated Mar. 24, 2016, 5 pages.

International Preliminary Report on Patentability for PCT/EP2015/053785, dated Feb. 8, 1016, 9 pages.

International Preliminary Report on Patentability for PCT/EP2016/055487, dated Sep. 19, 2017, 8 pages.

Majumdar et al., "Regioselective Aryl Radical Cyclization: Access to Pyrimidine-Annelated Spiro Heterocycles Through 5-exo Ring Closure," Synthesis 11:1864-1868 (2004).

Roppe et al., "5-[(2-Methyl-1,3-thiazol-4-yl)ethynyl]-2,3'-bipyridine: a highly potent, orally active metabotropic glutamate subtype 5 (mGluS) receptor antagonist with anxiolytic activity," Bioorg. Med. Chem. Lett. 14(15):3993-3996 (2004).

Vernon et al., "Additive neuroprotection by metabotropie glutamate receptor subtype-selective ligands in a rat Parkinson's model," Neuroreport 19(4):475-478 (2008).

International Search Report for PCT/EP2015/050127, dated Mar. 9, 2015, 3 pages.

International Search Report for PCT/EP2015/053785, dated May 8, 2015, 4 pages.

International Search Report for PCT/EP2016/055487, dated May 3, 2016, 5 pages.

International Search Report and Written Opinion for PCT/EP2016/066393, dated Oct. 19, 2016, 11 pages.

Guengerich, "A history of the roles of cytochrome P450 enzymes in the toxicity of drugs," Toxicol. Res. 37(1):1-23 (2021).

Hakkola et al., "Inhibition and induction of CYP enzymes in humans: an update," Arch. Toxicol. 94(11):3671-3722 (2020).

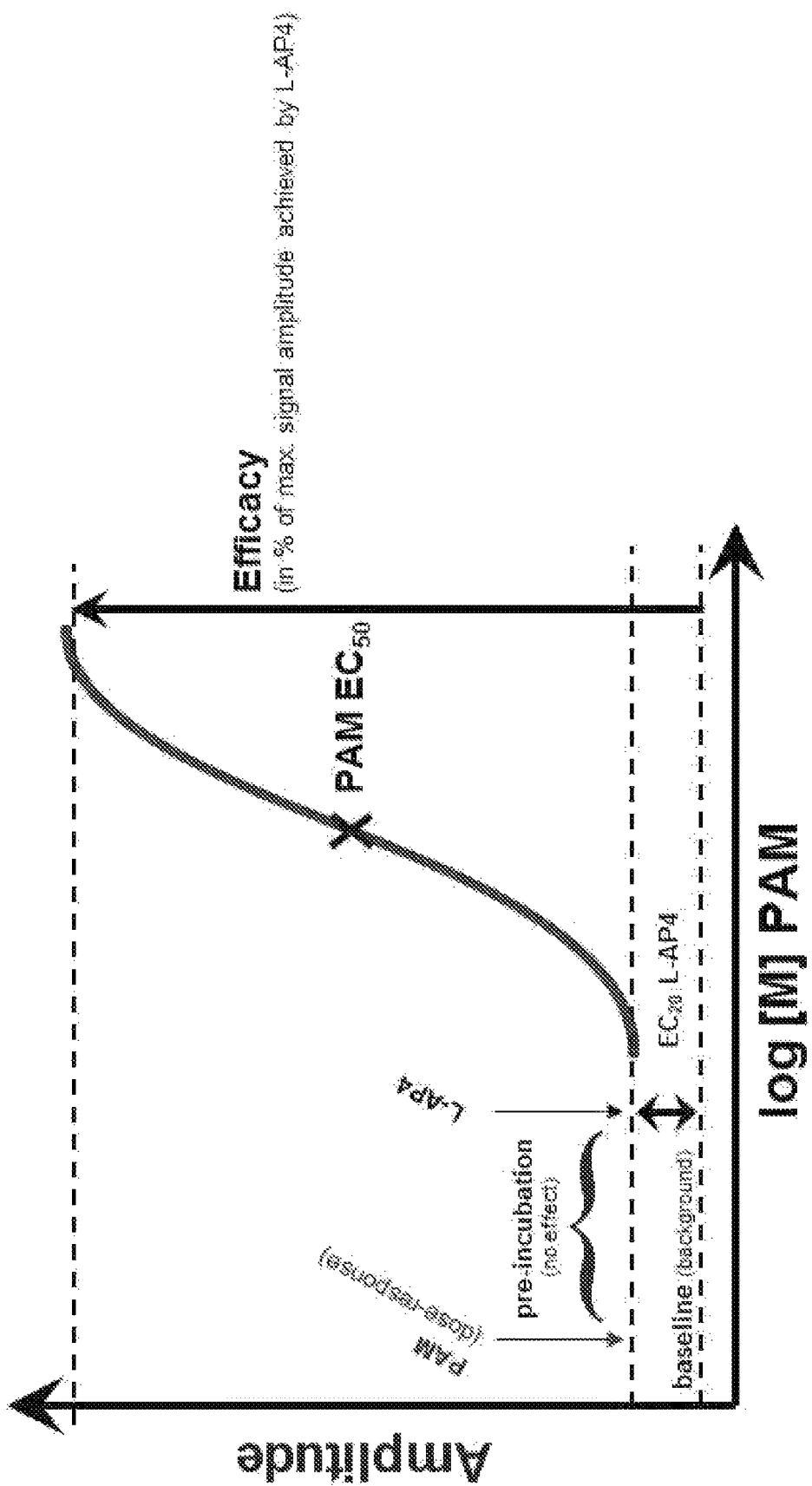

ETHYNYL DERIVATIVES

CROSS REFERENCE TO RELATED APPLICATIONS

This application is a continuation of U.S. application Ser. No. 16/250,278, filed Jan. 17, 2019, which is a continuation of International Application No. PCT/EP2017/067495, filed Jul. 12, 2017, which claims benefit of priority to European Application 16179837.6, filed Jul. 18, 2016, each of which is incorporated herein by reference in its entirety.

The present invention relates to compounds of formulas IA and IB

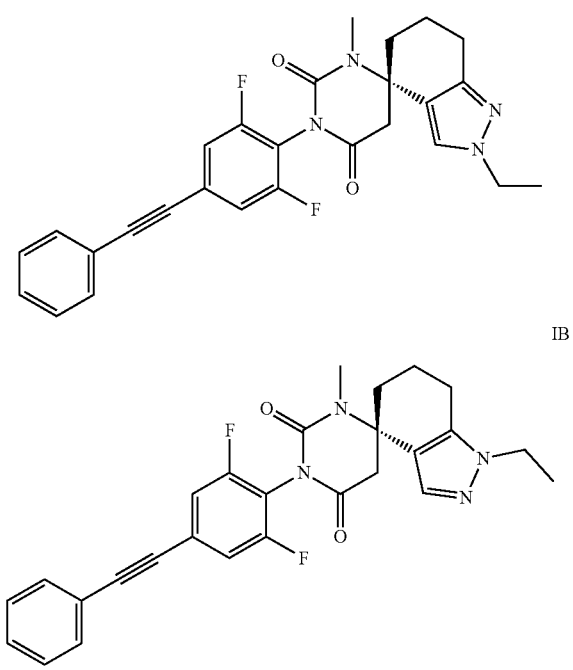

or to a pharmaceutically acceptable salt or acid addition salt, to a racemic mixture, or to its corresponding enantiomer and/or optical isomer and/or stereoisomer thereof.

It has been surprisingly found that the compounds of formulas IA and IB are positive allosteric modulators (PAMs) of metabotropic glutamate receptor 4 (mGluR4). Metabotropic glutamate receptor 4 is a protein that in humans is encoded by the GRM4 gene.

Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays a key modulatory role in many CNS and non-CNS pathways (*Celanire S, Campo B, Expert Opinion in Drug Discovery,* 2012)

The similarity in the ligand binding domains of group III mGluR's creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAMs are emerging as promising therapeutic agents for the treatment of motor (and non-motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias.

Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). These studies provide convincing preclinical evidence suggesting that mGluR4 activators constitute a valid approach not only for symptomatic treatments of PD, but also potentially as disease modifiers for this indication.

The neuroprotective effects of selective mGluR4 modulators was also described in *Neuroreport*, 19(4), 475-8, 2008, *Proc. Natl. Acad. Sci, USA,* 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (*Prediger R, et al. Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.,* 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology*, 46(2), 151-9, 2004).

In addition, mGluR4 modulators were also shown to be involved in glucagon secretion inhibition (*Diabetes*, 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research*, 11(9)3288-95, 2005). mGluR4 modulators may therefore have also potential role for the treatment of cancers.

Other proposed effects of mGluR4 PAM's can be expected for the treatment of emesis, obsessive compulsive disorder, anorexia and autism.

Compounds of formulas IA and IB are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, anorexia, autism, neuroprotection, cancer, depression and type 2 diabetes.

The present invention relates to compounds of formulas IA and IB and to their pharmaceutically acceptable salts, to these compounds as pharmaceutically active substances, to the processes for their production as well as to their use in the treatment or prevention of disorders, relating to allosteric modulators for the mGluR4 receptor, such as Parkinson's disease, anxiety, emesis, obsessive compulsive disorder, autism, neuroprotection, cancer, depression and diabetes type 2 and to pharmaceutical compositions containing the compounds of formula IA and IB.

A further object of the present invention is a method for the treatment or prophylaxis of Parkinson's disease, anxiety, emesis, obsessive compulsive disorder, anorexia, autism, neuroprotection, cancer, depression and type 2 diabetes, which method comprises administering an effective amount of a compound of formulas IA and IB to a mammal in need.

Furthermore, the invention includes all racemic mixtures, all their corresponding enantiomers and/or optical isomers, or analogues containing isotopes of hydrogen, fluorine, carbon, oxygen or nitrogen.

The term "pharmaceutically acceptable acid addition salt" embraces a salt with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid or p-toluenesulfonic acid.

The preparation of compounds of formulas IA and IB of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formulas IA and IB can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formulas IA and IB and their pharmaceutically acceptable salts may be prepared by methods, known in the art, for example by the process variant described below which process comprises alkylating a compound of formula

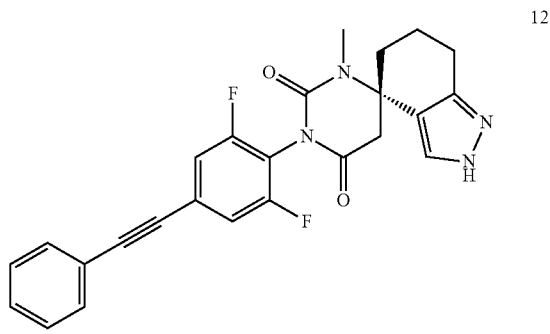 [SMILES: CN1C(=O)N(c2c(F)cc(C#Cc3ccccc3)cc2F)C(=O)C[C@]12CCCc1n[nH]cc12]

with ethyliodide and separating of the isomers to a compound of formulas

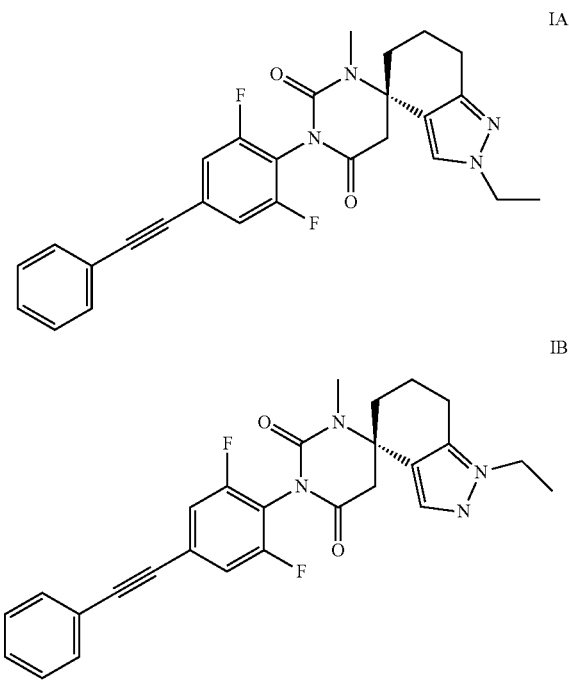

or, if desired, converting the compounds obtained into pharmaceutically acceptable salts thereof.

The preparation of compounds of formulas IA and IB is further described in more detail in scheme 1 and in examples 1-2.

Scheme 1

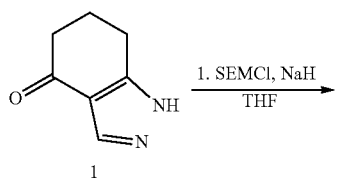

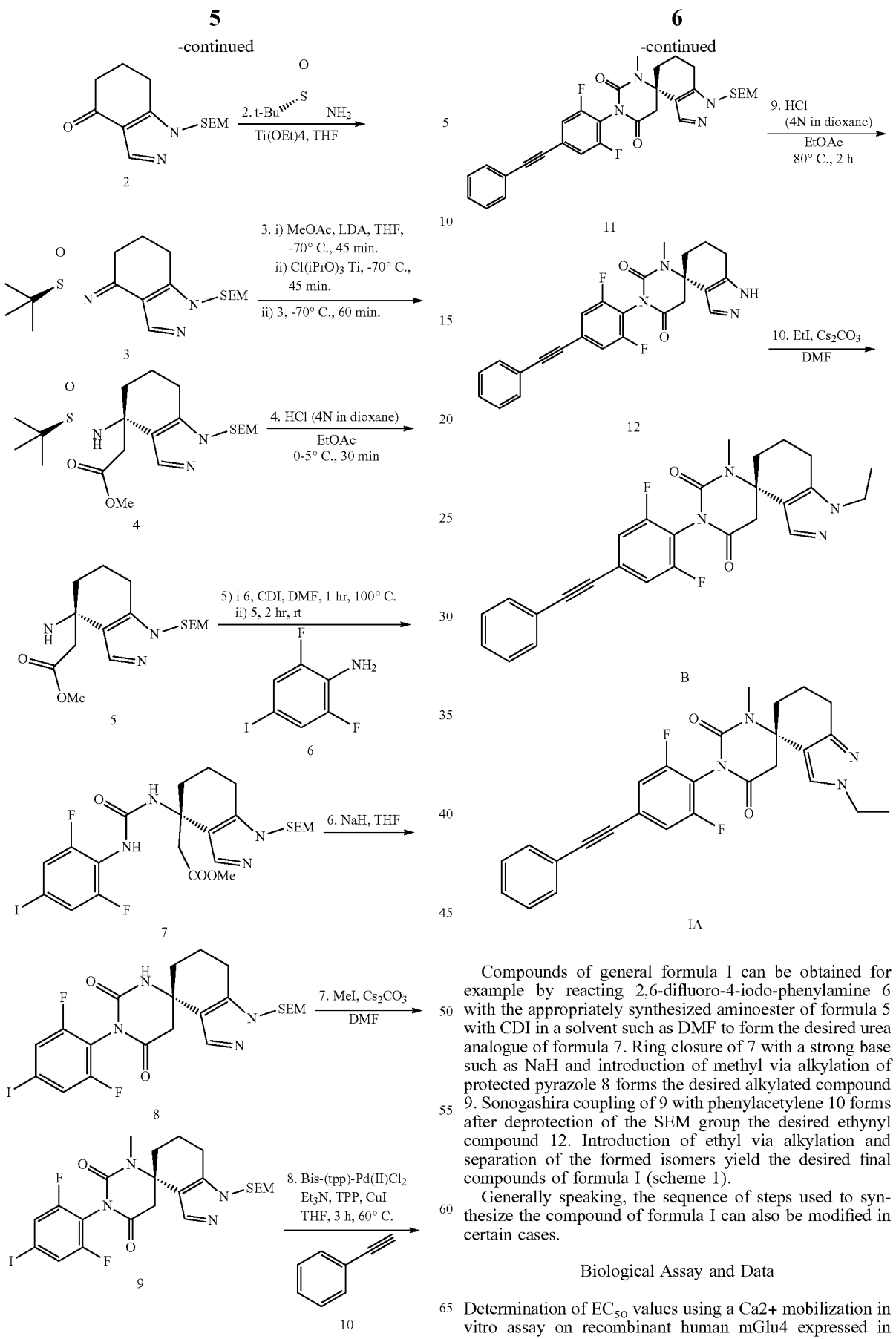

Compounds of general formula I can be obtained for example by reacting 2,6-difluoro-4-iodo-phenylamine 6 with the appropriately synthesized aminoester of formula 5 with CDI in a solvent such as DMF to form the desired urea analogue of formula 7. Ring closure of 7 with a strong base such as NaH and introduction of methyl via alkylation of protected pyrazole 8 forms the desired alkylated compound 9. Sonogashira coupling of 9 with phenylacetylene 10 forms after deprotection of the SEM group the desired ethynyl compound 12. Introduction of ethyl via alkylation and separation of the formed isomers yield the desired final compounds of formula I (scheme 1).

Generally speaking, the sequence of steps used to synthesize the compound of formula I can also be modified in certain cases.

Biological Assay and Data

Determination of $EC_{50}$ values using a Ca2+ mobilization in vitro assay on recombinant human mGlu4 expressed in HEK293 cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4 was indicative of an inhibitory activity of the test compound.

BRIEF DESCRIPTION OF THE FIGURE

FIG. 1: Illustration of the experimental outline for mGlu4 PAM Ca2+ mobilization screening assay and the determination of $EC_{50}$ and % Emax values.

LIST OF EXAMPLES AND DATA

| | Structure | Name | $EC_{50}$ (nM) mGlu4 PAM | Eff. (%) |
|---|---|---|---|---|
| 1 | 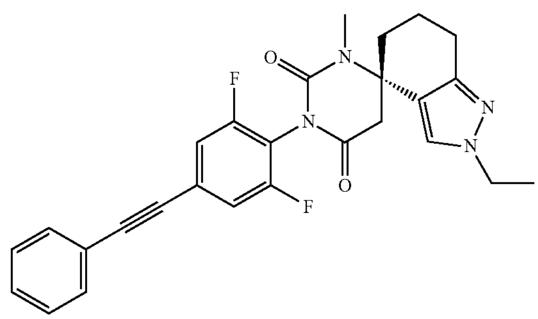 [SMILES: CCn1cc2c(n1)CCC[C@]21CC(=O)N(c2c(F)cc(C#Cc3ccccc3)cc2F)C(=O)N1C] | (4S)-3'-[2,6-Difluoro-4-(2-phenylethynyl)phenyl]-2-ethyl-1'-methyl-spiro[6,7-dihydro-5H-indazole-4,6'-hexahydropyrimidine]-2',4'-dione | 77 | 132 |
| 2 | 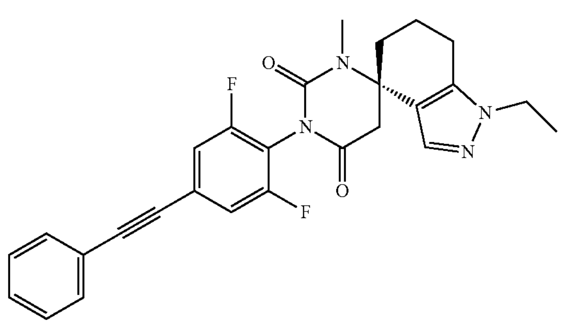 [SMILES: CCn1ncc2c1CCC[C@]21CC(=O)N(c2c(F)cc(C#Cc3ccccc3)cc2F)C(=O)N1C] | (4S)-3'-[2,6-Difluoro-4-(2-phenylethynyl)phenyl]-1-ethyl-1'-methyl-spiro[6,7-dihydro-5H-indazole-4,6'-hexahydropyrimidine]-2',4'-dione | 85 | 136 |

The compounds of formulas IA and IB and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formulas IA and IB and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula IA and IB, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formulas IA and IB or pharmaceutically acceptable salts thereof and a therapeutically inert excipient are also an object of the present invention, as is a process for the production of such medicaments which comprises bringing one or more compounds of formula IA and IB or pharmaceutically acceptable salts thereof and, if desired, one or more other therapeutically valuable substances into a galenical dosage form together with one or more therapeutically inert carriers.

As further mentioned earlier, the use of the compounds of formulas IA and IB for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the Following Composition are Manufactured in the Usual Manner:

| | mg/tablet | | | |
|---|---|---|---|---|
| ingredient | 5 | 25 | 100 | 500 |
| Compounds of formula IA or IB | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the Following Composition are Manufactured:

| | mg/capsule | | | |
|---|---|---|---|---|
| ingredient | 5 | 25 | 100 | 500 |
| Compound of formula IA or IB | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula IA or IB, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection Solutions of the Following Composition are Manufactured:

| ingredient | mg/injection solution. |
|---|---|
| Compound of formula IA or IB | 3 |
| Polyethylene Glycol 400 | 150 |
| acetic acid | q.s. ad pH 5.0 |
| water for injection solutions | ad 1.0 ml |

Manufacturing Procedure

A compound of formula IA or IB is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 1

(4S)-3'-[2,6-Difluoro-4-(2-phenylethynyl)phenyl]-2-ethyl-1'-methyl-spiro[6,7-dihydro-5H-indazole-4,6'-hexahydropyrimidine]-2',4'-dione

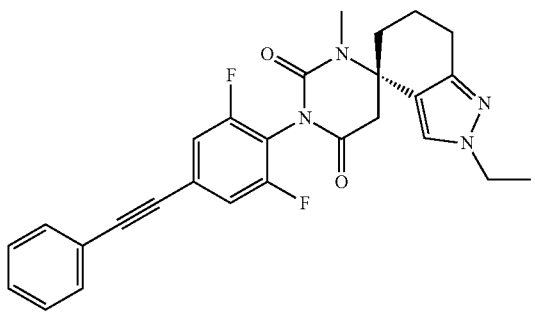 [SMILES: CCn1cc2c(n1)CCC[C@]21CC(=O)N(c2c(F)cc(C#Cc3ccccc3)cc2F)C(=O)N1C]

Step 1: 2-((2-(Trimethylsilyl)ethoxy)methyl)-6,7-dihydro-2H-indazol-4(5H)-one 6,7-Dihydro-2H-indazol-4(5H)-one (CAS 912259-10-0) (1.46 g, 10.7 mmol) was dissolved in THF (15 ml) and cooled to 0-5° C. Sodium hydride (60% dispersion in mineral oil) (450 mg, 11.3 mmol, 1.05 equiv.) was added carefully in portions and the mixture was stirred for 60 minutes at room temperature. The reaction mixture was cooled again to 0-5° C. and (2-(chloromethoxy)ethyl)trimethylsilane (2.28 ml, 2.15 g, 12.9 mmol, 1.2 equiv.) was added and the mixture was stirred for 2 hours at room temperature. The reaction mixture was extracted carefully with saturated NaHCO$_3$ solution and twice with ethyl acetate. The organic layers were washed with brine, dried over sodium sulfate and evaporated to dryness. The desired 2-((2-(trimethylsilyl)ethoxy)methyl)-6,7-dihydro-2H-indazol-4(5H)-one (quant. yield) was obtained as a yellow oil, MS: m/e=267.2 (M+H$^+$).

Step 2: (NE)-2-Methyl-N-[1-(2-trimethylsilylethoxymethyl)-6,7-dihydro-5H-indazol-4-ylidene]propane-2-sulfinamide 2-((2-(Trimethylsilyl)ethoxy)methyl)-6,7-dihydro-2H-indazol-4(5H)-one (Example 1, step 1) (40 g, 150.14 mmol) was dissolved in 400 ml of THF. (R)-2-Methylpropane-2-sulfinamide (CAS 196929-78-9) (27.3 g, 225.2 mmol, 1.5 equiv.) and titanium(IV) ethoxide (102.75 g, 93.4 ml, 450.42 mmol, 3.0 equiv.) were added and the mixture was stirred for 4 hours at 70° C. The reaction mixture was cooled and saturated NaHCO$_3$ solution and ethyl acetate were added. The formed suspension was filtered through celite and the filtrate was extracted twice with ethyl acetate. The organic layers were washed brine, dried over sodium sulfate and evaporated to dryness. The desired (NE)-2-methyl-N-[1-(2-trimethylsilylethoxymethyl)-6,7-dihydro-5H-indazol-4-ylidene]propane-2-sulfinamide (20.0 g, 36% yield) was obtained as a brown oil, MS: m/e=370.2 (M+H$^+$).

Step 3: Methyl 2-[(4S)-4-[[(R)-tert-butylsulfinyl]amino]-1-(2-trimethylsilylethoxymethyl)-6,7-dihydro-5H-indazol-4-yl]acetate Methyl acetate (22.25 g, 23.9 ml, 300.3 mmol, 3 equiv.) was dissolved in 370 ml of dry THF and the solution was cooled to −70° C. LDA (2.0 M in THF/heptane/ethylbenzene) (150 ml, 300.3 mmol, 3 equiv.) was added drop wise at −75° C. to −65° C. and the mixture was stirred for 45 minutes at −70° C. Chlorotitanium triisopropoxide (1.0 M in dichloromethane) (400 ml, 400 mmol, 4 equiv.) was added drop wise at −75° C. to −65° C. and the mixture was stirred for 45 minutes at −70° C. (NE)-2-methyl-N-[1-(2-trimethylsilylethoxymethyl)-6,7-dihydro-5H-indazol-4-ylidene]propane-2-sulfinamide (Example 1, step 2) (37 g, 100 mmol) dissolved in 370 ml of dry THF was added drop wise at −75° C. to −65° C. and the mixture was stirred for 1 hour at −70° C. Saturated NaHCO$_3$ solution was added and the mixture stirred for 10 minutes. Ethyl acetate was added to the formed suspension and the mixture was stirred for 10 minutes. The formed suspension was filtered through celite and the filtrate was extracted twice with ethyl acetate. The organic layers were washed with water and brine, dried over sodium sulfate and evaporated to dryness. The crude product was purified by flash chromatography. The desired methyl 2-[(4S)-4-[[(R)-tert-butyl sulfinyl]amino]-1-(2- trimethylsilylethoxymethyl)-6,7-dihydro-5H- indazol-4-yl]acetate (22 g, 40% yield) was obtained as a brown oil, MS: m/e=444.2 (M+H$^+$).

Step 4: Methyl 2-[(4S)-4-amino-1-(2-trimethylsilylethoxymethyl)-6,7-dihydro-5H-indazol-4-yl]acetate Methyl 2-[(4S)-4-[[(R)-tert-butylsulfinyl]amino]-1-(2-trimethylsilylethoxymethyl)-6,7-dihydro-5H-indazol-4-yl]acetate (Example 1, step 3) (20 g, 45.08 mmol) was dissolved in 500 ml of ethyl acetate and HCl (4N in ethyl acetate) (56.3 ml, 225.4 mmol, 5 equiv.) was added drop wise at 0-5° C. The mixture was stirred for 30 minutes at 0-5° C. The reaction mixture was evaporated at 0-5° C. and extracted with saturated NaHCO$_3$ solution and three times with dichloromethane. The organic layers were combined, dried over sodium sulfate and evaporated to dryness. The desired methyl 2-[(4S)-4-amino-1-(2-trimethylsilylethoxymethyl)-6,7-dihydro-5H-indazol-4-yl]acetate (340 mg, 54% yield) was obtained as a yellow oil, MS: m/e=340.1 (M+H$^+$).

Step 5: Methyl 2-[(4S)-4-[(2,6-difluoro-4-iodo-phenyl)carbamoylamino]-1-(2-trimethylsilylethoxymethyl)-6,7-dihydro-5H-indazol- 4-yl]acetate 2,6-Difluoro-4-iodoaniline (14.4 g, 56.56 mmol, 1.2 equiv.) was dissolved in DMF (250 ml) and CDI (9.17 g, 56.56 mmol, 1.2 equiv.) was added at room temperature. The mixture was stirred for 1 hour at 100° C. To the mixture methyl 2-[(4S)-4-amino-1-(2-trimethylsilylethoxymethyl)-6,7-dihydro-5H-indazol-4-yl]acetate (Example 1, step 4) (16 g, 47.13 mmol, 1.0 equiv.) dissolved in 20 ml of DMF was added at room temperature and the mixture was stirred for 2 hours at room temperature. The reaction mixture was poured into water and extracted three times with ethyl acetate. The organic layers were washed with water and brine, dried over sodium sulfate and evaporated to dryness. The crude product was purified by flash chromatography. The desired methyl 2-[(4S)-4-[(2,6-difluoro-4-iodo-phenyl)carbamoylamino]-1-(2-trimethylsilylethoxymethyl)-6,7-dihydro-5H-indazol-4- yl]acetate (9.1 g, 19% yield) was obtained as a brown gum, MS: m/e=621.1 (M+H$^+$).

Step 6: (4S)-3'-(2,6-Difluoro-4-iodo-phenyl)-1-(2-trimethylsilylethoxymethyl)spiro[6,7-dihydro-5H-indazole-4,6'-hexahydropyrimidine]-2',4'-dione (18 g, 29.01 mmol) Methyl 2-[(4S)-4-[(2,6-difluoro-4-iodo-phenyl)carbamoylamino]-1-(2-trimethylsilylethoxymethyl)-6,7-dihydro- 5H-indazol-4-yl]acetate (Example 1, step 5) was dissolved in THF (360 ml) and sodium hydride (60% in mineral oil) (1.74 g, 43.52 mmol, 1.5 equiv.) was added at 0-5° C. The mixture was stirred for 1 hour at room temperature. The reaction mixture was extracted with saturated NH$_4$Cl solution and three times with ethyl acetate. The organic layers were washed with brine, dried over sodium sulfate and evaporated to dryness. The desired (4S)-3'-(2,6-difluoro-4-iodo-phenyl)-1-(2-trimethyl silylethoxymethyl) spiro[6,7-dihydro-5H-indazole-4,6'- hexahydropyrimidine]-2',4'-dione (240 mg, 86% yield) was obtained as a yellow gum, MS: m/e=589.0 (M+H$^+$).

Step 7: (4S)-3'-(2,6-Difluoro-4-iodo-phenyl)-1'-methyl-1-(2-trimethylsilylethoxymethyl)spiro[6,7-dihydro-5H-indazole-4,6'-hexahydropyrimidine]-2',4'-dione (17 g, 28.9 mmol) (4S)-3'-(2,6-Difluoro-4-iodo-phenyl)-1-(2-trimethylsilylethoxymethyl)spiro[6,7-dihydro-5H-indazole-4,6'-hexahydropyrimidine]-2',4'-dione (Example 1, step 6) was dissolved in DMF (200 ml) and cesium carbonate (14.12 g, 43.34 mmol, 1.5 equiv.) and iodomethane (4.92 g, 2.16 ml, 34.67 mmol, 1.2 equiv.) were added at room temperature. The mixture was stirred for 1 hour at room temperature. The reaction mixture was poured into water and extracted three times with ethyl acetate. The organic layers were washed with water and brine, dried over sodium sulfate and evaporated to dryness. The crude product was purified by flash chromatography on a silica gel column eluting with an petroleum:ethyl acetate 10:1 to 1:1 gradient. The desired (4S)-3'-(2,6-difluoro-4-iodo-phenyl)-1'-methyl-1-(2-trimethylsilylethoxymethyl)spiro[6,7-dihydro-5H-indazole-4,6'-hexahydropyrimidine]-2',4'-dione (15.7 g, 90% yield) was obtained as a yellow gum, MS: m/e=603.2 (M+H$^+$).

Step 8: (4S)-3'-[2,6-Difluoro-4-(2-phenylethynyl)phenyl]-1'-methyl-1-(2-trimethylsilylethoxymethyl)spiro[6,7-dihydro-5H-indazole-4,6'-hexahydropyrimidine]-2',4'-dione (4S)-3'-(2,6-Difluoro-4-iodo-phenyl)-1'-methyl-1-(2-trimethylsilylethoxymethyl)spiro[6,7-dihydro-5H-indazole-4,6'-hexahydropyrimidine]-2',4'-dione (Example 1, step 7) (12 g, 19.9 mmol) and phenylacetylene (3.05 g, 3.32 ml, 29.9 mmol, 1.5 equiv.) were dissolved in 120 ml of THF. Triethylamine (10.1 g, 13.9 ml, 99.6 mmol, 5 equiv.), bis-(triphenylphosphine)-palladium(II)dichloride (420 mg, 0.6 mmol, 0.03 equiv.), triphenylphosphine (313 mg, 1.2 mmol, 0.06 equiv.) and copper(I)iodide (114 mg, 0.6 mmol, 0.03 equiv.) were added and the mixture was stirred for 3 hours at 60° C. The reaction mixture was evaporated with isolute®. The crude product was purified by flash chromatography on a silica gel column eluting with an ethyl acetate:heptane 30:70 to 100:0 gradient. The desired (4S)-3'-[2,6-difluoro-4-(2-phenylethynyl)phenyl]-1'-methyl-1-(2-trimethylsilylethoxymethyl)spiro[6,7-dihydro-5H-indazole-4,6'-hexahydropyrimidine]-2',4'-dione (11.2 g, 98% yield) was obtained as a brown foam, MS: m/e=577.3 (M+H$^+$).

Step 9: (4S)-3'-[2,6-Difluoro-4-(2-phenylethynyl)phenyl]-1'-methyl-spiro[1,5,6,7-tetrahydroindazole-4,6'- hexahydropyrimidine]-2',4'-dione The title compound was obtained as a white foam, MS: m/e=447.2 (M+H$^+$), using chemistry similar to that described in Example 1, step 4 by stirring the reaction for 2 hours at 80° C. starting from (S)-1'-(2,6-difluoro-4-(phenylethynyl)phenyl)-3'-methyl-2-((2-(trimethylsilyl)ethoxy)methyl)-2,5,6,7-tetrahydro-1'H-spiro[indazole- 4,4'-pyrimidine]-2',6'(3'H,5'H)-dione (Example 1, step 8).

Step 10: (4S)-3'-[2,6-Difluoro-4-(2-phenylethynyl)phenyl]-2-ethyl-1'-methyl-spiro[6,7-dihydro-5H-indazole-4,6'-hexahydropyrimidine]-2',4'-dione The title compound was obtained as a white solid, MS: m/e=475.4 (M+H$^+$), using chemistry similar to that described in Example 1, step 7 starting from (4S)-3'-[2,6-difluoro-4-(2-phenylethynyl)phenyl]-1'-methyl-spiro[1,5,6,7-tetrahydroindazole-4,6'-hexahydropyrimidine]-2',4'-dione (Example 1, step 9) and iodoethane. The desired (4S)-3'-[2, 6-difluoro-4-(2-phenylethynyl)phenyl]-2-ethyl-1'-methyl-spiro[6,7-dihydro-5H-indazole-4,6'-hexahydropyrimidine]-2',4'-dione was obtained by separation of the two formed isomers using a Reprosil Chiral NR® column with heptane: ethanol 60:40 mixture as eluent collecting peak A.

Example 2

(4S)-3'-[2,6-Difluoro-4-(2-phenylethynyl)phenyl]-1-ethyl-1'-methyl-spiro[6,7-dihydro-5H-indazole-4,6'-hexahydropyrimidine]-2',4'-dione

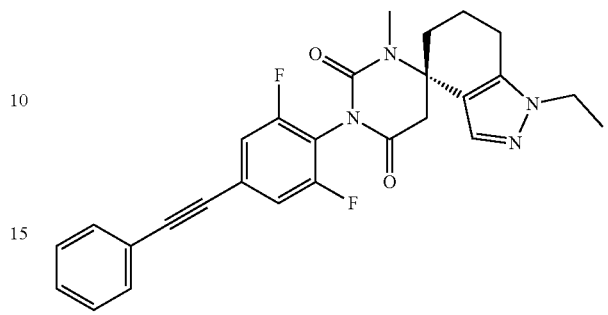

The title compound was obtained as a white solid, MS: m/e=475.4 (M+H$^+$), using chemistry similar to that described in Example 1, step 7 starting from (4S)-3'-[2,6-difluoro-4-(2-phenylethynyl)phenyl]-1'-methyl-spiro[1,5,6, 7-tetrahydroindazole-4,6'-hexahydropyrimidine]-2',4'-dione (Example 1, step 9) and iodoethane. The desired (4S)-3'-[2, 6-difluoro-4-(2-phenylethynyl)phenyl]-1-ethyl-1'-methyl-spiro[6,7-dihydro-5H-indazole-4,6'-hexahydropyrimidine]-2',4'-dione (Example 1, step 9) and iodoethane. The desired (4S)-3 '-[2,6-difluoro-4-(2-phenylethynyl)phenyl]-1-ethyl-1'-methyl-spiro[6,7-dihydro-5H-indazole-4,6'-hexahydropyrimidine]-2',4'-dione was obtained by separation of the two formed isomers using a Reprosil Chiral NR® column with heptane:ethanol 60:40 mixture as eluent collecting peak B.

The invention claimed is:
1. A compound of formula IB:

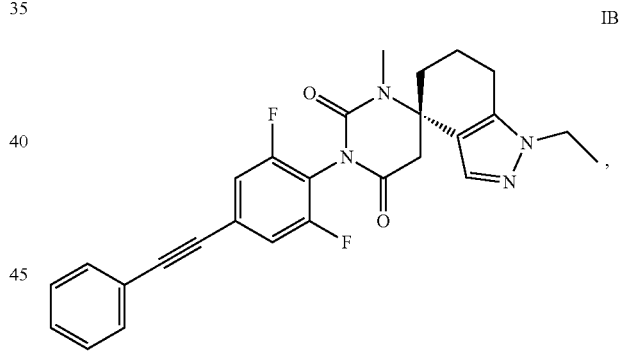

or a pharmaceutically acceptable salt or acid addition salt or stereoisomer thereof.

2. A process for the manufacture of a compound of claim 1, wherein the process comprises: alkylating a compound of formula 12:

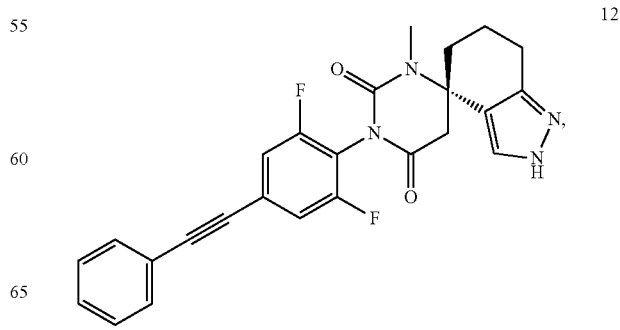

with ethyliodide; and separating of the isomers to a compound of formula IB:

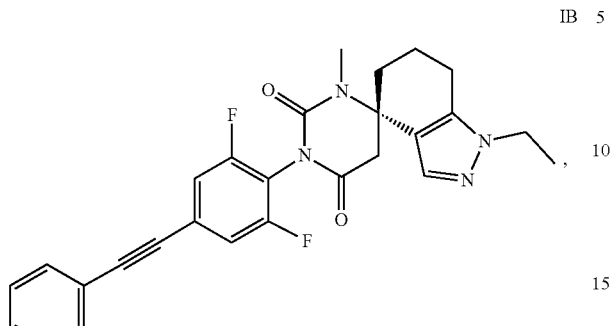

or optionally converting the compound obtained into a pharmaceutically acceptable salt or acid addition salt thereof.

3. A pharmaceutical composition comprising a compound of claim 1, or a pharmaceutically acceptable salt or acid addition salt or stereoismer thereof, and a pharmaceutically acceptable excipient.

4. A method for the treatment of Parkinson's disease in a patient, wherein the method comprises administering an effective amount of a compound of claim 1, or a pharmaceutically acceptable salt or acid addition salt or stereoisomer thereof, to the patient in need thereof.

* * * * *